United States Patent
Koo et al.

(10) Patent No.: US 10,605,816 B1
(45) Date of Patent: Mar. 31, 2020

(54) H-FIELD IMAGER FOR ASSAYS

(71) Applicant: Maxim Integrated Products, Inc., Sunnyvale, CA (US)

(72) Inventors: Ronald B. Koo, Los Altos, CA (US); Henry Grage, Johns Creek, GA (US)

(73) Assignee: MAXIM INTEGRATED PRODUCTS, INC., San Jose, CA (US)

( * ) Notice: Subject to any disclaimer, the term of this patent is extended or adjusted under 35 U.S.C. 154(b) by 594 days.

(21) Appl. No.: 14/972,857

(22) Filed: Dec. 17, 2015

Related U.S. Application Data

(60) Provisional application No. 62/203,637, filed on Aug. 11, 2015.

(51) Int. Cl.
*G01N 35/00* (2006.01)
*G01N 33/543* (2006.01)

(52) U.S. Cl.
CPC ... *G01N 35/0098* (2013.01); *G01N 33/54333* (2013.01)

(58) Field of Classification Search
None
See application file for complete search history.

(56) References Cited

U.S. PATENT DOCUMENTS

| | | | |
|---|---|---|---|
| 2004/0246479 A1* | 12/2004 | Cartlidge | G01N 21/6458 356/335 |
| 2006/0261431 A1 | 11/2006 | Kim et al. | |
| 2010/0019155 A1 | 1/2010 | Klunder et al. | |
| 2013/0265459 A1 | 10/2013 | Duparre et al. | |
| 2014/0001058 A1 | 1/2014 | Ghaffari et al. | |
| 2015/0219732 A1* | 8/2015 | Diamond | A61B 5/04008 324/201 |
| 2015/0293060 A1 | 10/2015 | Jacobsen | |
| 2015/0301031 A1 | 10/2015 | Zin et al. | |
| 2016/0245788 A1 | 8/2016 | Wang et al. | |
| 2017/0038282 A1 | 2/2017 | Veiseh et al. | |

OTHER PUBLICATIONS

Zhao et al. ("NFC-WISP: A sensing and computationally enhanced near-field RFID platform," 2015 IEEE International Conference on RFID (RFID), San Diego, CA, 2015, pp. 174-181).*

Gambini, Simone et al., "A CMOS 10kpixel Baseline-Free Magnetic Bead Detector with Column-Parallel Readout for Miniaturized Immunoassays", IEEE International Solid-State Circuits Conference, ISSCC 2012, Session 6, Medical, Displays and Imagers / 6.9, pp. 126-127 and Annotated die photo.

(Continued)

*Primary Examiner* — Rebecca L Martinez
(74) *Attorney, Agent, or Firm* — Kevin E. West; Advent, LLP

(57) ABSTRACT

This disclosure describes a magnetic-field image sensor and method of use. In accordance with implementations of the magnetic-field image sensor, a sample can be placed on top of the magnetic field image sensor. An image of the magnetic nanoparticles or superparamagnetic nanoparticles can be created immediately afterwards based upon detection of a change in magnetic field caused by the magnetic nanoparticles or superparamagnetic nanoparticles. From this image, computer imaging algorithms can determine attributes (e.g., size, shape, type, quantity, distribution, etc.) of the target entity.

8 Claims, 7 Drawing Sheets

(56) References Cited

OTHER PUBLICATIONS

Liu, Paul Peng et al., "Magnetic Relaxation Detector for Microbead Labels", IEEE Journal of Solid-State Circuits, vol. 47, No. 4, Apr. 2012, pp. 1056-1064.

Murali, Pramod et al., "A CMOS Micro-Flow Cytometer for Magnetic Label Detection and Classification", IEEE International Solid-State Circuits Conference, ISSCC 2014, Session 24, Integrated Biomedical Systems / 24.6, pp. 422-423 and Chip micrograph photo.

Laborde C., et al., "Realtime Imaging of Microparticles and Living Cells With CMOS Nanocapacitor Arrays," Nature Nanotechnology, Aug. 2015, vol. 10, pp. 791-795.

Non-Final Office Action dated Jun. 14, 2018, for U.S. Appl. No. 15/956,299.

Non-Final Office Action for U.S. Appl. No. 15/688,449 dated Jul. 3, 2018.

Widdershoven F. et al., "CMOS biosensor platform" IEEE 9781424474196110, 2010, pp. 36.1.1-36.1.4.

Wong C. C., et al., "S based High Density Micro Array Platform for Electrochemical Detection and Enumeration of Cells," IEEE International Electron Devices Meeting, 2013, pp. 373-376.

\* cited by examiner

H-FIELD IMAGER FOR ASSAYS

BACKGROUND

Assays are important for diagnosis because they can indicate bacterial infections, viral infections, poisoning, overdose, and so forth. Most assays have to be done in a laboratory and cannot be done in the home, where patients can benefit from the convenience and the privacy. To be effective in Third World countries where medical doctors and laboratories are scarce, the assays need to be done anywhere and anytime. Similarly, in times of disaster or in a war zone, the same mobile requirements must be met.

The reason that most assays cannot be mobile is that stationary machines perform the analysis. These machines can be cabinet size down to bench top size. They are expensive and need AC wall power. The technology in the machines (e.g., flow cytometry, polymerase chain reaction, immunoassays, etc.) is poorly suited to be converted into a mobile implementation.

In recent years, mobile assays have been developed to detect influenza and Human Immunodeficiency Virus (HIV). These tests are qualitative and cannot provide a quantitative measurement of the entity in question. For example, the therapy for a human with HIV is based upon its concentration.

SUMMARY

This disclosure describes a magnetic-field image sensor and method of use. In accordance with implementations of the magnetic-field image sensor, sample including functionalized magnetic nanoparticles (e.g., mixed with functionalized magnetic nanoparticles) can be placed on top of a magnetic-field image sensor. An image of the magnetic nanoparticles can be created immediately afterwards based upon detection of a change in magnetic field caused by the magnetic nanoparticles. From this image, computer imaging algorithms can determine attributes (e.g., size, shape, type, quantity, distribution, etc.) of cells, viruses, and other entities.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Figure 1:
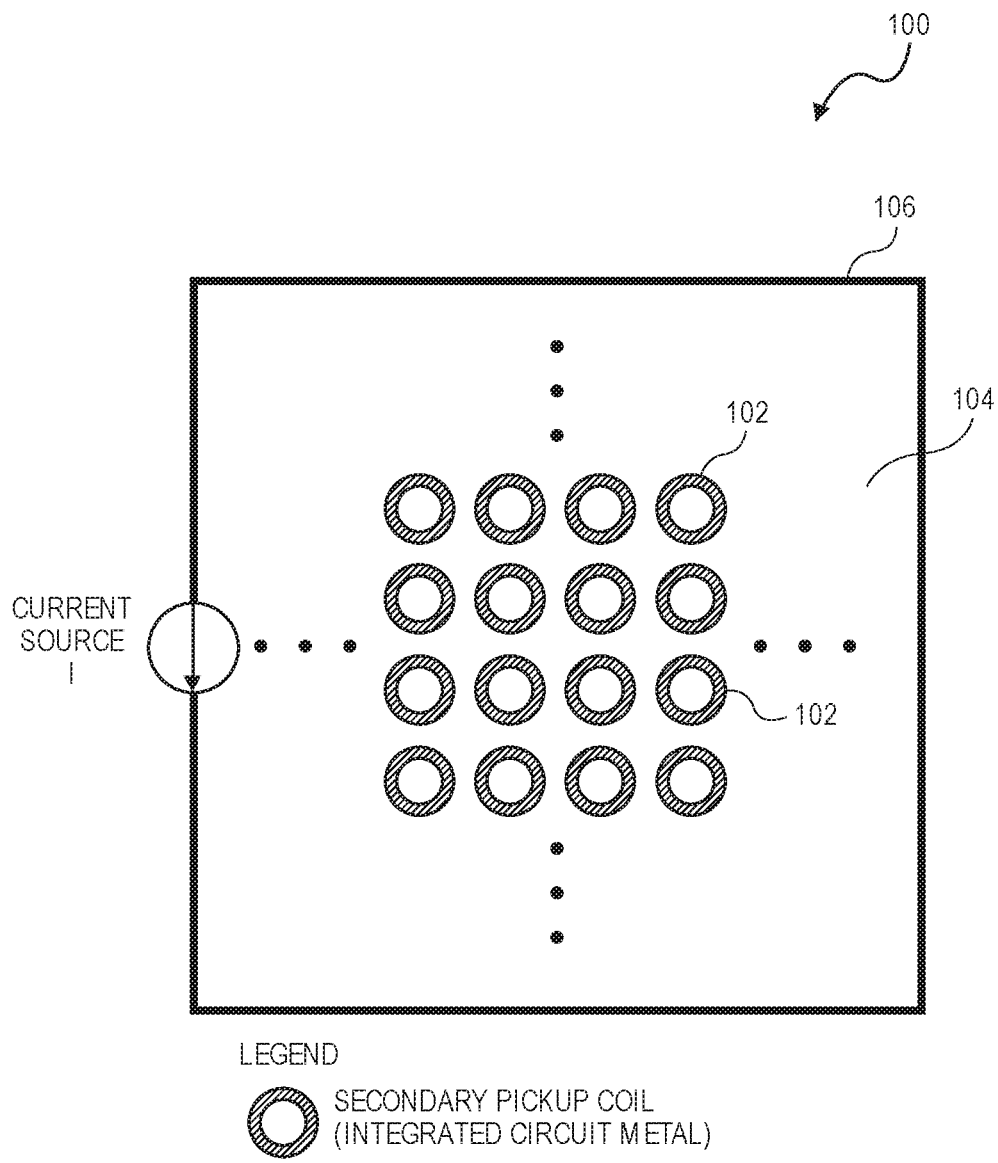
FIGS. 1 through 4B are diagrammatic views of a magnetic-field image sensor implemented in accordance with embodiments of the present disclosure.

A pixel-based image sensor is disclosed in which respective pixels of an array of pixels senses changes in the magnetic field above the respective pixel to determine the presence and amount of magnetic nanoparticles or superparamagnetic nanoparticles. From this information, attributes, such as size, type, morphology, distribution, number of the target entity can be deduced. In embodiments, the pitch of the pixels can vary from 40 nm to 100 µm. Each pixel can be configured to detect a change in magnetic field proximate to the respective pixel. In some embodiments, the sensor is implemented as an integrated circuit. The sensor can also be formed from patterned or printed conductors on a substrate such as glass or plastic, where at least one integrated circuit electrically connected to the pixels can be configured to measure the change in magnetic field. The magnetic-field image sensor is well suited to be implemented in a mobile test because it is small, low power, low cost, and disposable. For example, the resulting mobile detection or measurement device that includes a magnetic field image sensor may have dimensions that range from about four centimeters (4 cm) by about two centimeters (2 cm) by about one millimeter (1 mm) to about twenty centimeters (20 cm) by about five centimeters (5 cm) by about one centimeter (1 cm). Thus, the magnetic-field image sensor can be utilized in a number of environmental settings. For instance, the magnetic-field image sensor may be utilized in an indoor environment, in a hostile environment, in an outdoors environment, or the like.

Example Implementations

FIG. 1 illustrates a magnetic-field (H-Field) image sensor 100 in accordance with various embodiments of this disclosure. Those skilled in the art will appreciate that the embodiments illustrated in the drawings and/or described herein may be fully or partially combined to result in additional embodiments. Accordingly, the illustrated and described embodiments should be understood as explanatory and not as limitations of the present disclosure.

In an embodiment illustrated in FIG. 1, a magnetic field image sensor 100 is shown to include a plurality of coils 102 (e.g., an array of coils deployed through the magnetic field image sensor 100) for detecting changes in magnetic fields. Each coil 102 can define a pixel within the magnetic field image sensor 100. For instance, the array of coils 102 defines an active sensor area where a fluid sample including cells, viruses, and other entities can be deposited over such that respective coils 102 can detect a change in the magnetic field caused by magnetic nanoparticles or superparamagnetic nanoparticles. In one or more implementations, the pitch between respective coils 102 can vary from 40 nanometers to 100 micrometers.

In embodiments, the image sensor 100 includes a layer 104. The layer 104 is utilized to physically separate the cells, viruses, and other entities from the coils 102. In implementations, the layer 104 comprises any suitable material (e.g., an integrated circuit passivation layer, glass panel, or plastic substrate) that allows the coils 102 to detect a change in magnetic field caused by magnetic nanoparticles or superparamagnetic nanoparticles.

As shown in FIG. 1, the image sensor 100 includes a primary excitation coil 106 disposed about the panel 104. The primary excitation coil 106 causes generation of a magnetic field that is perpendicular to a plane defined by the panel 104 when current flows through the primary excitation coil 106. If magnetic nanoparticles are in the sample, then they will rotate such that their magnetic moments will be aligned parallel to the magnetic field. If superparamagnetic nanoparticles are in the sample, then the magnetic field generated by the primary excitation coil 106 induces magnetism in the superparamagnetic nanoparticles, which align their resulting magnetic moments parallel to the magnetic field. In addition, the magnetic field interacts with the magnetic moment of the magnetic nanoparticles or the superparamagnetic nanoparticles and pulls them to the plane of the magnetic field image sensor.

Figure 2:
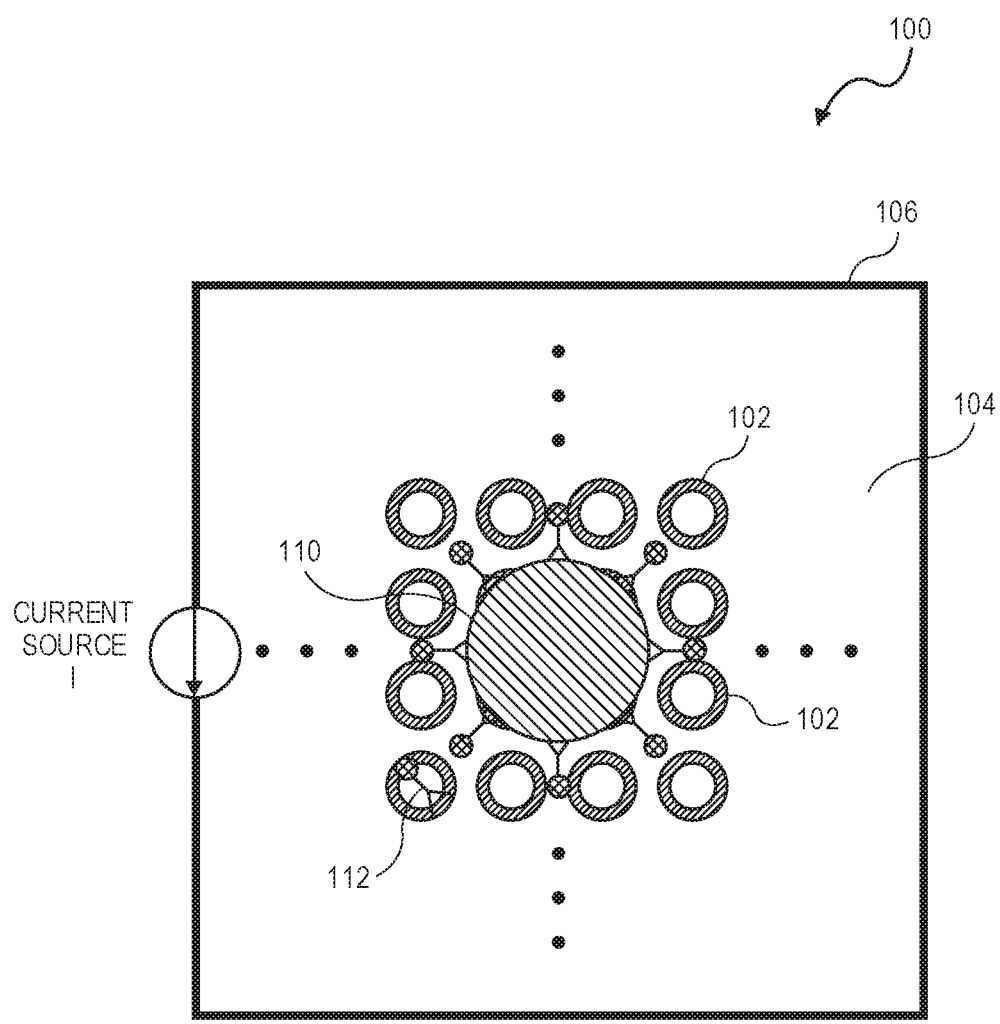

In the embodiment shown in FIG. 2, the magnetic field image sensor is used to count the number of cells 110 in a sample. The target cells might be infectious bacteria in whole human blood. Super paramagnetic nanoparticles functionalized with antibodies 112 that bind to structures on the target cell can be mixed into the sample. The super paramagnetic nanoparticles attach to the target cells. Once the primary excitation coil 106 is turned on, then the super paramagnetic nanoparticles align themselves to the primary magnetic field. The nanoparticles are pulled to the image sensor, which senses the presence and amount of nanoparticles on a pixel-by-pixel basis. Target cells have a much higher number of nanoparticles attached to it than can be found elsewhere in the sample. Suitable algorithms can interpret the resulting image frame to determine the number of cells for a given sample volume.

Figure 3A:
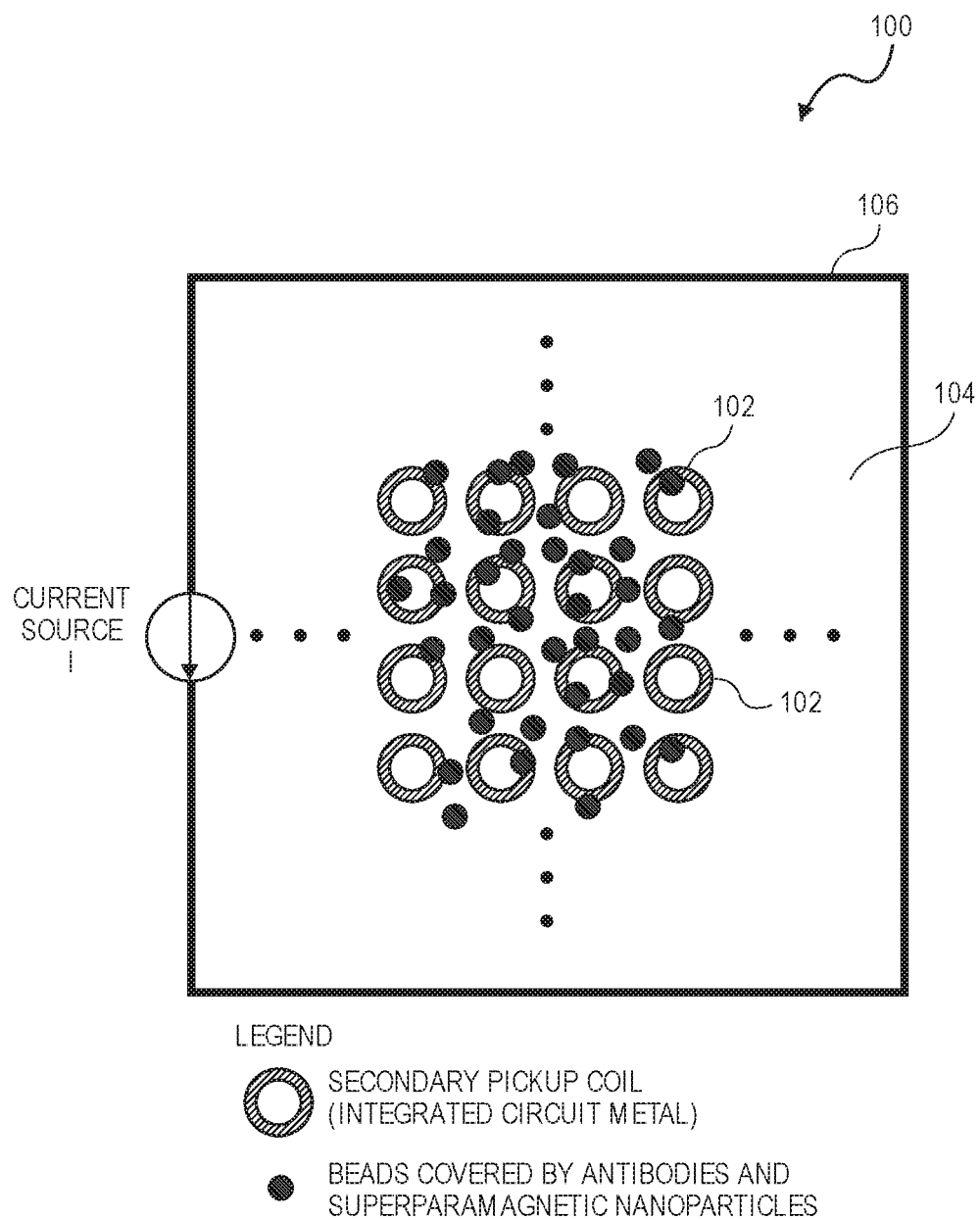
Figure 3B:
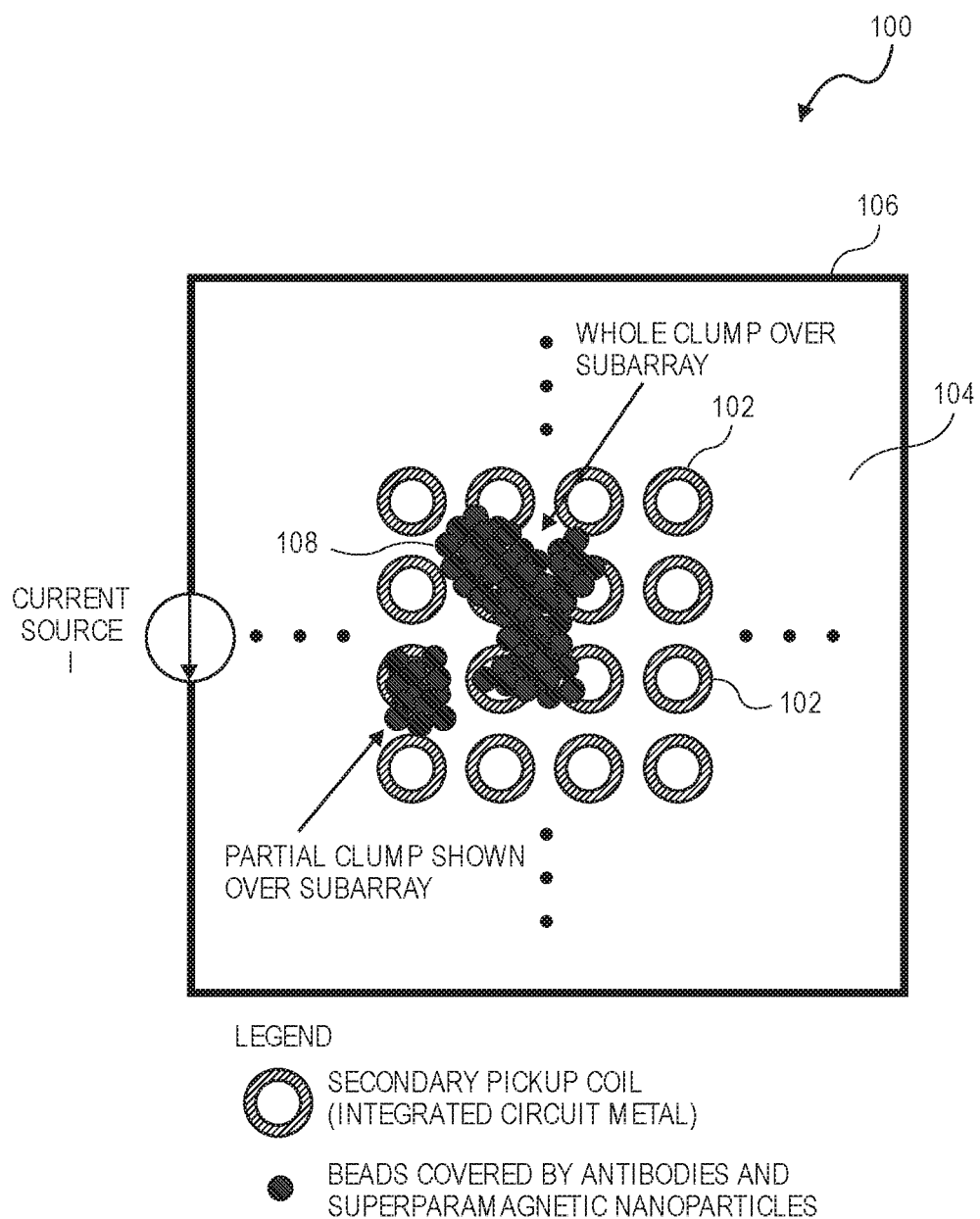

Referring to FIGS. 3A and 3B, in an agglutination assay, beads that are covered with superparamagnetic nanoparticles functionalized with agents that have an affinity for the target entity are mixed into the sample.

If the target entity is present in the sample, then the beads clump together at a rate dependent upon the concentration of the target entity in the sample. As shown in FIG. 3B, clumps 108 of beads may extend over portions of one or more coils 102 (e.g., pixels). In one or more implementations, one or more coils 102 detect a change in the magnetic field as a result of the clumps 108 being directly disposed over the respective coils 102. For example, adjacent coils 102 may detect a change in a magnetic field due to a clump 108 being located directly over the adjacent coils indicating the presence and the density of superparamagnetic nanoparticles. For example, the image sensor 100 may determine a presence and density of superparamagnetic nanoparticles based upon the number of adjacent coils 102 detecting a change in magnetic field due to the location of the clumps 108 with respect to the adjacent coils 102.

Figure 4A:
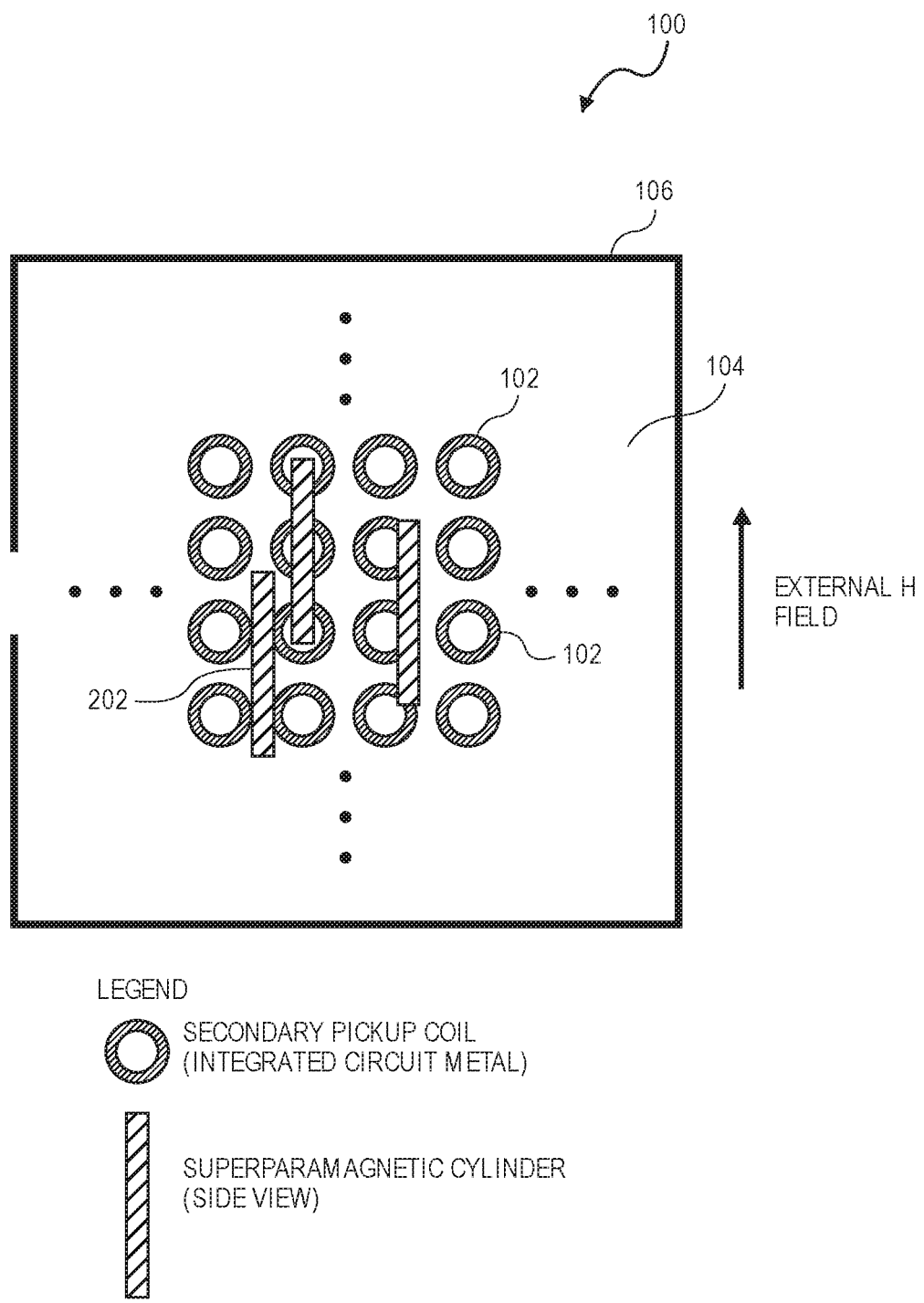
Figure 4B:
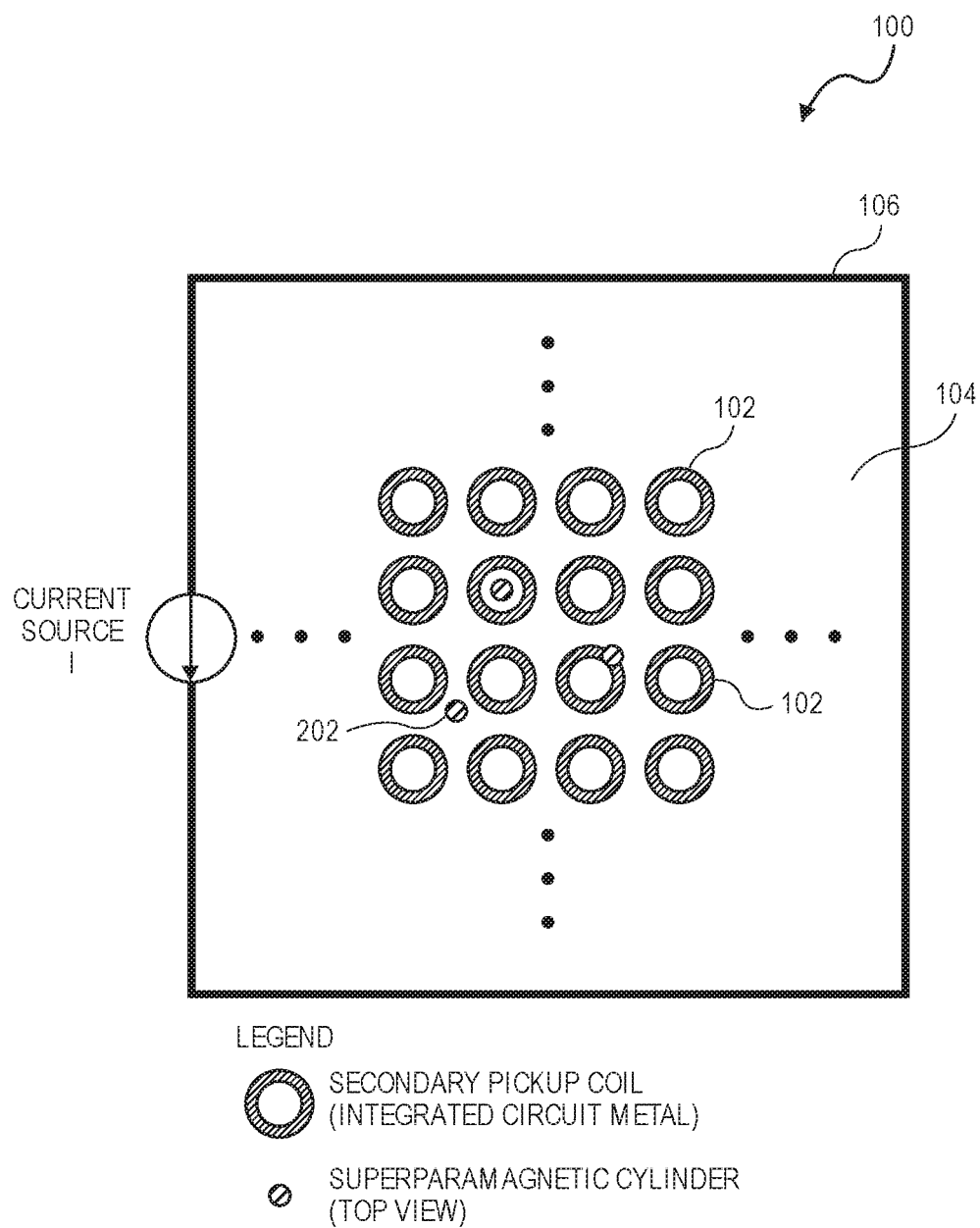

In another implementation of a coagulation assay, as shown in FIGS. 4A and 4B, a biological sample, such as a blood sample, may be disposed over the panel 104 of the image sensor 100. In this implementation, superparamagnetic cylinders 202 can be added to the biological sample. An external magnetic field that is parallel to a plane defined by the panel 104 can be generated that causes the superparamagnetic cylinders 202 to align parallel with respect to the surface of the panel 104. In one or more implementations, one or more attributes of the biological sample can be determined. For example, a coagulation measurement of the biological can be determined by terminating the external magnetic field and causing current to flow through the primary excitation coil 106, which causes generation of a magnetic field that is perpendicular to the surface of the panel 104. The magnetic field perpendicular to the surface of the panel 104 causes the superparamagnetic cylinders 202 to transition from at least substantially parallel with respect to the surface of the panel 104 to at least substantially perpendicular with respect to the surface of the panel 104. One or more coils 102 detect the changes in magnetic field as the super paramagnetic cylinder rotates from parallel to perpendicular with respect to the surface of the panel 104. In one or more implementations, the image sensor 100 measures a time ranging from the termination of the external magnetic field to the detecting a presence of the superparamagnetic cylinder 202 due to it being at least substantially perpendicular to the surface of the panel 104. Based upon the measured time, the image sensor 100 can determine a coagulation characteristic of the biological sample.

The image sensor 100 may further include processing logic embodied by a programmable logic device, a controller/microcontroller, a single or multiple core processor, an ASIC, or the like. The processing logic may be configured to generate an image based on changes in the magnetic field detected by one or more coils 102. In embodiments, the processing logic can include fast Fourier transform (FFT) and magnetic field detection algorithms. The processing logic can further include one or more computer imaging software modules executable by a processor/controller to identify attributes of cells/particles (e.g., superparamagnetic nanoparticles) in the generated magnetic-field image. For example, the computer imaging modules may cause the processor/controller to perform a comparison between one or more portions of the generated magnetic-field image and a library with stored images or data associated with one or more attributes, such as size, type, morphology, distribution, number of cells, and so forth.

In some embodiments, the image sensor 100 can be configured to collect multiple magnetic-field images taken at different times (e.g., time lapsed images) to monitor growth or movement of superparamagnetic nanoparticles (or magnetic nanoparticles). For example, time lapsed images from an agglutination assay can be used to monitor movement of dispersed particles (e.g., antibody-coated beads) as they agglutinate in the presence of an antigen.

In various embodiments of the present disclosure, the image sensor 100 may be at least partially powered by a near-field communications (NFC) device. For instance, a mobile electronic device (e.g., a smart phone) having NFC technology may be positioned proximate to the image sensor 100. Due to the proximity to the NFC technology of the mobile electronic device, the image sensor 100 may be at least partially powered by the NFC technology.

Example Processes

Figure 5:
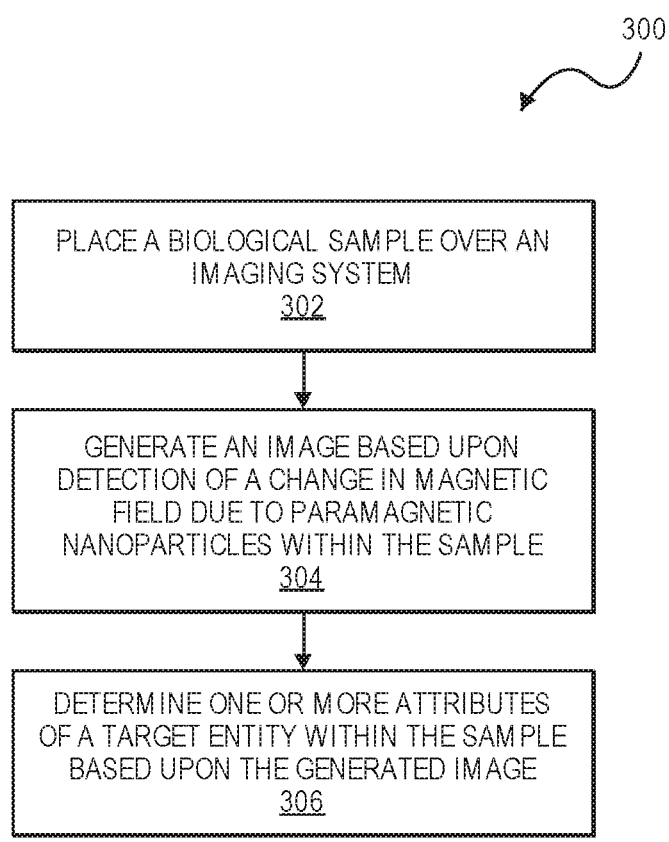
FIG. 5 is flow diagram illustrating a method of imaging magnetic nanoparticles or superparamagnetic nanoparticles in a fluid sample with a magnetic-field image sensor in accordance with present disclosure.

FIG. 5 shows a flow diagram for a method 300 of imaging biological cells or viruses with a magnetic-field image sensor, such as the image sensor 100 described herein. Accordingly, the method 300 may include any steps or operations that are described herein with regard to the magnetic-field image sensor 100 or that are necessary for achieving an attribute of the magnetic-field image sensor 100 that is described herein. However, the method 300 is in no way limited to any embodiment of the magnetic-field image sensor 100 described herein.

As shown in FIG. 5, the method 300 can include: placing a sample on a panel disposed over a plurality of coils (e.g., image sensor 100), the sample including a fluid containing a target entity and functionalized super paramagnetic nanoparticles with an agent that has an affinity for the target entity (Block 302); generating an image based upon detection of a change in magnetic field due to the super paramagnetic nanoparticles (or paramagnetic nanoparticles) proximity to one or more coils (Block 304); and determining one or more attributes of the target entity based upon the generated image (Block 306). In some implementations, determining the one or more attributes of the target entity based upon the generated image can include performance of a comparison between one or more portions of the generated image with a library of stored images or data structures. For example, computer imaging algorithms may be executed by one or more processors to perform comparisons with a library of stored images or parameters to determine attributes of the target entity including one or more of: size, type, morphology, distribution, immunoassay characteristics, or number of cells.

In some implementations, the magnetic-based sensor can include multiple active sensor areas or regions (e.g., as discussed above with regard to image sensor 100) with different respective sensor pitches suitable for detecting differently sized particles (or different ranges of particles sizes). The method can further include as step of selecting a first sensor area or a second sensor area based upon a size of a virus or cell being imaged.

Those skilled in the art will appreciate that the forgoing steps can be carried out in any order, unless otherwise indicated herein, and that one or more steps may be carried out substantially simultaneously or at least partially in parallel. It should be further recognized that the various functions, operations, blocks, or steps described throughout the present disclosure may be carried out by any combination of hardware, software, or firmware. Various steps or operations may be carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, the cloud, or any other suitable device. In general, the terms "controller" and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. An image sensor for performing an assay, the image sensor comprising:
   a primary excitation coil configured to generate a primary magnetic field; and
   a plurality of secondary coils, each of the plurality of secondary coils defining a pixel within the image sensor; and
   an integrated circuit electrically connected to the plurality of secondary coils and configured to detect a change in a local magnetic field proximate at least one of the secondary coils thereby enabling detection of the presence of at least one of the magnetic nanoparticles and the superparamagnetic nanoparticles in a sample disposed adjacent the plurality of secondary coils on a pixel by pixel basis.

2. The image sensor of claim 1, further comprising a panel,
   the panel disposed between the sample and the plurality of secondary coils.

3. The image sensor of claim 2, wherein the panel comprises a glass material.

4. The image sensor of claim 1, further comprising a processor communicatively coupled to the plurality of secondary coils and configure to generate an image based upon the detected change in the local magnetic field by at least one of the plurality of secondary coils, the image representing one or more attributes of the sample.

5. The image sensor of claim 4, wherein the processor further determines one or more attributes of the sample based upon the generated image.

6. The image sensor of claim 1, wherein the image sensor can be utilized in a plurality of environmental settings, the plurality of environmental settings including at least one of a hostile environment, an indoor environment, or an outdoor environment.

7. The image sensor of claim 1, wherein the image sensor is at least partially powered by a near field communications (NFC) module.

8. The image sensor of claim 1, wherein the resulting mobile detection or measurement device that includes a magnetic field image sensor comprises dimensions ranging from about four centimeters (4 cm) by about two centimeters (2 cm) by about one millimeter (1 mm) to about twenty centimeters (20 cm) by about five centimeters (5 cm) by about one centimeter (1 cm).

* * * * *